United States Patent [19]
Monn et al.

[11] Patent Number: 6,143,783
[45] Date of Patent: Nov. 7, 2000

[54] EXCITATORY AMINO ACID RECEPTOR MODULATORS

[75] Inventors: James Allen Monn, Indianapolis; Matthew John Valli, Zionsville, both of Ind.

[73] Assignee: Eli Lilly and Company, Indianapolis, Ind.

[21] Appl. No.: 09/438,764

[22] Filed: Nov. 11, 1999

Related U.S. Application Data

[60] Provisional application No. 60/108,371, Nov. 13, 1998.

[51] Int. Cl.$^7$ .......................... C07C 61/13; C07C 61/29; A61K 31/195; A61K 31/225
[52] U.S. Cl. .......................... 514/533; 514/563; 514/564; 560/119; 562/501
[58] Field of Search .......................... 560/119; 562/501; 514/533, 563, 564

[56] References Cited

U.S. PATENT DOCUMENTS

| | | | |
|---|---|---|---|
| 5,688,826 | 11/1997 | Massey et al. | 514/443 |
| 5,750,566 | 5/1998 | Monn et al. | 514/510 |
| 5,912,248 | 6/1999 | Fernandez et al. | 514/256 |
| 5,916,920 | 6/1999 | Fernandez et al. | 514/561 |
| 5,958,960 | 9/1999 | Massey et al. | 514/393 |

FOREIGN PATENT DOCUMENTS

| | | | |
|---|---|---|---|
| 0 774 454 A1 | 5/1997 | European Pat. Off. | C07C 229/50 |
| 0 878 463 A1 | 11/1998 | European Pat. Off. | C07C 229/50 |

*Primary Examiner*—Howard C. Lee
*Assistant Examiner*—Leigh C. Maier
*Attorney, Agent, or Firm*—Suzanne M. Harvey; Arvie J. Anderson

[57] ABSTRACT

The present invention relates to compounds of the formula

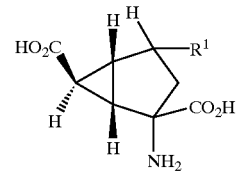

in which $R^1$ is defined in the specification, and non-toxic metabolically labile esters and amides thereof are useful as modulators of metabotropic glutamate receptor function.

4 Claims, No Drawings

EXCITATORY AMINO ACID RECEPTOR MODULATORS

CROSS REFERENCE

This application claims priority of Provisional Application Ser. No. 60/108,371, filed Nov. 13, 1998.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), -amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D or C, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and anti-emetic agents.

International Patent Application Publication No. WO 96/05175 discloses the compound 2-aminobicyclo[3.1.0] hexane-2,6-dicarboxylic acid and its salts and esters as metabotropic glutamate receptor agonists.

The present invention provides a compound of formula

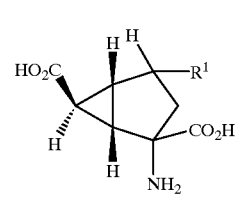

(I)

in which $R^1$ represents $NO_2$; or a non-toxic metabolically labile ester or amide thereof; or a pharmaceutically acceptable salt thereof.

The compounds of formula I are modulators of metabotropic glutamate receptor function, in particular agonists or antagonists of glutamate at metabotropic glutamate receptors.

According to another aspect, therefore, the present invention provides a method of modulating metabotropic glutamate receptor function in a mammal including a human, which comprises administering an effective amount of a compound of formula I, or a non-toxic metabolically labile ester or amide thereof, or a pharmaceutically acceptable salt thereof.

As used herein, the term "mammal" is defined as any warm blooded animal such as, but not limited to, a mouse, guinea pig, dog, horse, or human. Preferably, the mammal is human.

According to yet another aspect, the present invention provides the use of a compound of formula I as defined hereinabove for the manufacture of a medicament for use in modulating metabotropic glutamate receptor function.

It will be appreciated that the compounds of formula I contain five asymmetric carbon atoms; three being in the cyclopropane ring and two being in the cyclopentane ring. The present invention includes all stereoisomeric forms of the compounds of formula I, including each of the individual enantiomers and mixtures thereof.

The present invention also includes all physical forms of the compounds of formula I, including crystalline solvates.

Preferably the compounds of formula I have the configuration Ia or Ib shown below

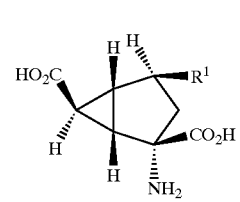

Ia

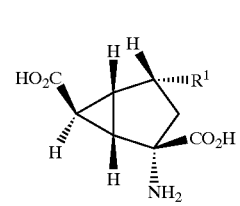

Ib

A particularly preferred compound of formula I includes (1S*2S*4R*5R*6S*) 2-Amino-4-nitrobicyclo[3.1.0] hexane-2,6-dicarboxylic acid.

The present invention includes pharmaceutically acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, butyne-1,4-dioate, hexane-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, a-hydroxybutyrate, glycolate, maleate, tartrate, methane-sulfonate, propanesulfonate, naphthalene-1-sulfonate, naphthalene-2-sulfonate, mandelate, magnesium, tetramethyl-ammonium, potassium, trimethylammonium, sodium, methyl-ammonium, calcium, and the like salts.

As used herein, the terms "halide" or "halo" refer to chlorine, bromine or iodine.

Pharmaceutically acceptable metabolically labile ester and amide of compounds of formula I are ester or amide derivatives of compounds of formula I that are hydrolyzed in vivo to afford said compound of formula I and a pharmaceutically acceptable alcohol or amine. Examples of metabolically labile esters include esters formed with (1–6C) alkanols in which the alkanol moiety may be optionally substituted by a (1–8C) alkoxy group, for example methanol, ethanol, propanol and methoxyethanol. Example of metabolically labile amides include amides formed with amines such as methylamine.

The compounds of formula I can be prepared by techniques and procedures readily available to, one of ordinary skill in the art, for example by following the procedures as set forth in the following schemes. These schemes are not intended to limit the scope of the invention in any way. All substituents, unless otherwise indicated, are previously defined. The reagents and starting materials are readily available to one of ordinary skill in the art. Scheme I provides a synthesis of compounds of Formula I.

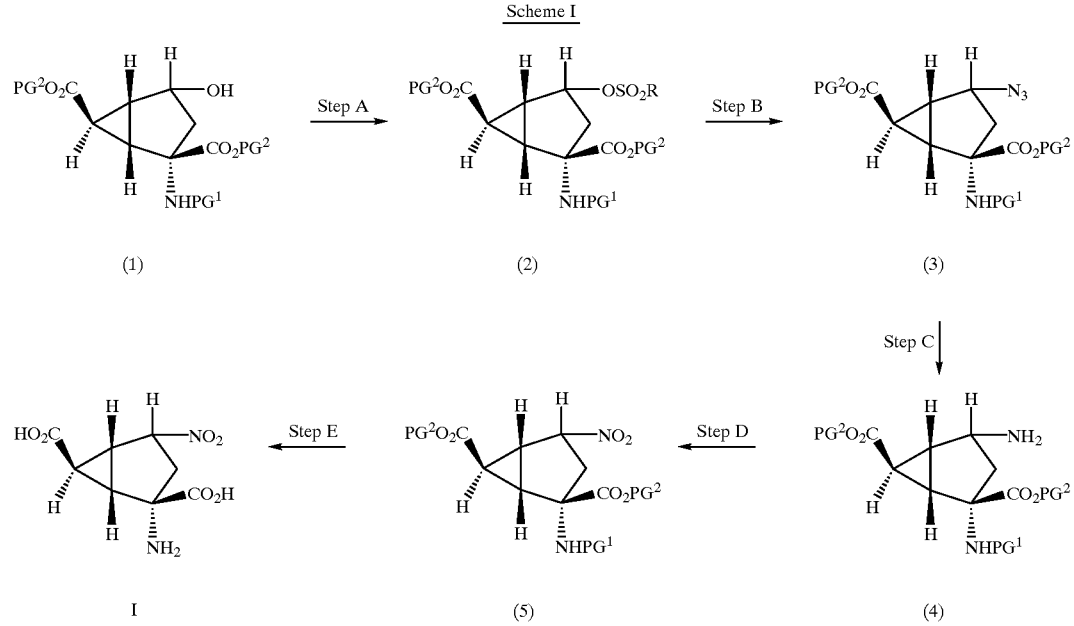

$PG^1$ is an amine protecting group.
$PG^2$ is a carboxy protecting group.
R is an alkyl group, aryl group, p-methylphenyl, or perfluoroalkyl, such as p-methylphenyl, phenyl, methyl and trifluoromethyl.

In Scheme I, step A, the compound of structure (2) may be prepared by reacting the compound of structure (1) with a hydrocarbonylsulfonyl halide such as p-toluenesulfonyl chloride or methanesulfonyl chloride, for example in pyridine as reaction solvent. The reaction is conveniently performed at room temperature. The product is then isolated and purified by extraction techniques and chromatography well-known in the art.

In Scheme I, step B, the compound of structure (3) may be prepared by reacting the compound of structure (2) with an azide salt, such as sodium azide, for example. The reaction is performed in a solvent such as dimethylsulfoxide at a temperature in the range of from about 0° to 50° C.

In Scheme I, step C, the compound of structure (4) may be prepared by reducing a compound of structure (3). For example, the reduction can be performed using triphenylphosphine in the presence of an aqueous ether, such as aqueous tetrahydrofuran at a temperature in the range of from about 0° to 100° C. The product is then isolated and purified by extraction techniques and chromatography well-known in the art.

In Scheme I, step D, the amine of structure (4), is oxidized to the nitro derivative of structure (5). This oxidation is well documented in the literature. For example, it has been accomplished utilizing mCPBA (Wiberg, K. B., et al., *J Org Chem.,* 58(6), p. 1372, 1993. Greven, R., Juetten, P., Scharf, H-D. *J Org Chem.,* 58(14), p. 3742, 1993.), MeReO$_3$/H$_2$O$_2$ (Murray, R. W., et al. *Tet Let,* 37(6), p. 805, 1996), ozone (Rainer, H., and Scharf, H-D., *Liebigs Ann Chem,* 2, p. 117, 1993), t-BuOOH (Suresh, et al. *Tetrahedron,* 51(41), p.11305, 1995), dimethyldioxirane, (Murray, R. W., Singh, M., Rath, N., *Tet Assym,* 7(6), p.1611, 1996), KMnO$_4$, or F$_2$ in CH$_3$ CN/H$_2$O (Rozen, S., and Kol, M., *J Org Chem.,* 57(26), p.7342, 1992. Rozen, S., Bar-Haim, A., Mischani, E., *J Org Chem.,* 59(5), p. 1208, 1994.) This intermediate can then be hydrolyzed to the final product as outlined below.

Alternatively, the compound of structure (5) can be prepared directly from the compound of structure (3) by methods documented in the literature. For example, treatment of compound of structure (3) with either PPh$_3$ or PBu$_3$ followed by an oxidant, for example ozone, will provide compound of structure (5)(Corey E. J., Samuelsson, B., Luzzio, F. A., *J. Am. Chem. Soc.,* 106(12), p. 3682, 1984; Wade, P. A., Kondracki, P. A., Carroll, P. J., *J. Am. Chem. Soc.,* 113(23), pp. 8807–8811, 1991.). Alternatively, this transformation can be effected by treatment with oxygen and ultraviolet irradiation (Ishikawa, S., Tsuji, S., Sawaki, Y., *J. Am. Chem. Soc.,* 113(11), pp. 4282–4288, 1991.)

In Scheme 1, step E, the compounds of structure (5) are readily deprotected by one of ordinary skill in the art, wherein PG$^1$ and PG$^2$ can be removed either sequentially or concomitantly. For example, an alkyl carboxyl protecting group may be removed by hydrolysis. The hydrolysis may conveniently be performed by stirring a solution of the compound of structure (5) and either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range of from about 10° to 300° C.

In addition, an benzyl carboxyl protecting group may conveniently be removed by hydrogenation. The hydrogenation may conveniently be effected by reacting the protected compound with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° to 100° C.

An acyl, amine protecting group is also conveniently removed by hydrolysis, for example as described for the removal of an alkyl carboxyl protecting group. A t-butoxycarbonyl group is conveniently removed using anhydrous hydrogen chloride in a solvent such as ethyl acetate.

It is to be appreciated that the deprotection can be carried out in any manner which gives the final product of formula I, including sequential removal of the carboxy and amino protecting groups.

The compounds of formula I may be resolved using conventional methods, for example by forming a crystalline salt with an optically active acid or base. Alternatively, optically active starting materials may be used to prepare compounds of formula I in optically pure form.

It is also to be appreciated that, if necessary and/or desired, the compound of formula I may be converted into a non-toxic metabolically labile ester or amide thereof; and/or; the compound of formula I or a non-toxic metabolically labile ester or amide thereof may be converted into a pharmaceutically acceptable salt thereof.

The compound of structure (1) may be prepared from a compound of structure

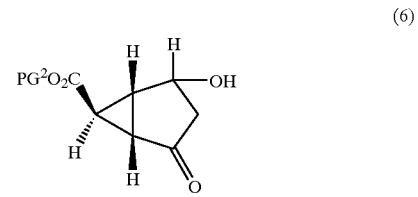

(6)

by formation of the hydantoin, hydrolysis and protection. For example, reacting a compound of structure (6) with an alkali metal cyanide, such as lithium, sodium or potassium cyanide, and ammonium carbonate in an aqueous alcohol, such as aqueous ethanol. Conveniently the reaction is performed at a temperature in the range of from about 35° to 150° C. The hydantoins obtained are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from about 500° to 150° C.

The protection of carboxylic acid and amine groups is generally described in McOmie, Protecting Groups in Organic Chemistry, Plenum Press, N.Y., 1973, and Greene and Wuts, Protecting Groups in Organic Synthesis, 2nd. Ed., John Wiley & Sons, N.Y., 1991. Examples of carboxy protecting groups include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl. Examples of amine protecting groups include acyl groups, such as groups of formula R$^a$CO in which R$^a$ represents (1–6C) alkyl, (3–10C) cycloalkyl, phenyl(1–6C) alkyl, phenyl, (1–6C) alkoxy, such as t-butoxy, phenyl(1–6C)alkoxy, or a (3–10C) cycloalkoxy, wherein a phenyl group may optionally be substituted by one or two substituents independently selected from amino, hydroxy, nitro, halogeno, (1–6C) alkyl, (1–6C) alkoxy, carboxy, (1–6C) alkoxycarbonyl, carbamoyl, (1–6C) alkanoylamino, (1–6C) alkylsulphonylamino, phenylsulphonylamino, toluenesulphonyl-amino, and (1–6C) fluoroalkyl.

The compounds of structure (6) may be prepared by reacting a compound of structure (7)

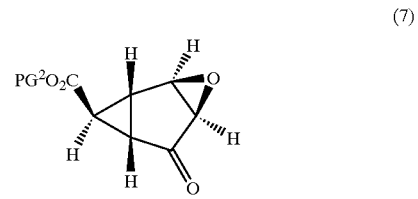

(7)

with a thiol, such as N-acetyl-L-cysteine, a base, such as sodium borate and a diaryldiselenide, such as diphenyldiselenide.

The compounds of structure (7) may be prepared by reacting a compound of structure (8)

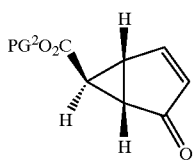

(8)

with a peroxide, such as tert-butyl hydroperoxide in the presence of a base, for example, DBU. A suitable solvent for the reaction includes tetrahydrofuran.

The compounds of structure (8) may be prepared by reacting a compound of structure (9)

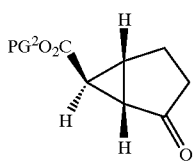

(9)

with iodotrimethyl silane in the presence of triethylamine to afford a silyl enol ether, and then reacting the silyl enol ether with palladium acetate. Alternatively, they may be prepared by reacting a compound of structure (9) with allyl methyl carbonate in the presence of palladium(II)acetate. The reaction is conveniently performed in anhydrous acetonitrile.

The compounds of structure 9 are known and may be prepared by reacting 2-cyclopenten-1-one with a carboxy protected (dimethyl sulfuranylidene) acetate. Suitable solvents for the reaction include aromatic hydrocarbons, such as toluene. The desired diastereomeric product may be isolated by chromatography.

In the schemes above, preferred values for $PG^2$ when the designation represents esterified carboxyl groups are (1–6C) alkoxycarbonyl groups such as ethoxycarbonyl.

Likewise, a preferred value for $PG^1$ is t-butoxycarbonyl.

The effective amount or dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester or amide thereof, or a pharmaceutically acceptable salt thereof.

The formula I compounds of the present invention are also believed to have the ability to treat a variety of other neurological disorders in mammals that are associated with glutamate dysfunction, including muscular spasms, convulsions, migraine headaches, urinary incontinence, nicotine withdrawal, psychosis, (such as schizophrenia) opiate tolerance and withdrawal, anxiety, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester or amide thereof, or a pharmaceutically acceptable salt thereof.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., *Neuropharmacol.*, 1996, 35, 1661–1672 and 1997, 36, 1–11).

The compounds of the present invention are preferably formulated prior to administration. Therefore, another aspect of the present invention is a pharmaceutical formulation comprising a compound of formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The following Examples further illustrate the compounds of the present invention and the methods for their synthesis.

The following abbreviations are used in the following: EtOAc, ethyl acetate; THF, tetrahydrofuran; Boc, t-butoxycarbonyl; Boc$_2$O, t-butoxycarboxylic acid anhydride; EtOH, ethanol; TsCl, p-toluenesulfonyl chloride; Et$_2$O, diethyl ether; DBU, 1,8-diazabicyclo[5.4.0]-undec-7-ene; and FDMS, field desorption mass spectrometry.

Preparation 1

Carboethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88–90° C.

Preparation 2

(1S*,5R*,6S*) Ethyl 2-Oxobicyclo[3.1.0]hexane-6-carboxylate

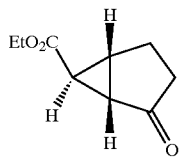

A suspension of carboethoxymethyl dimethylsulfonium bromide (45.5 g, 198.6 mmol) in toluene (350 mL) was treated with 1,8-diazabicyclo[5.4.0]undec-7-ene (30.2 g, 198.4 mmol). The resulting mixture was stirred at room temperature. After one hour, the reaction mixture was treated with 2-cyclopenten-1-one (19.57 g, 238.4 mmol). After an additional 18 hours, the reaction mixture was added to a 1 N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g (68%) of the title compound. Melting point: 36–38° C.

FDMS: m/z=168 (M+)

Analysis calculated for C$_9$H$_{12}$O$_3$: C, 64.27; H, 7.19. Found: C, 64.54; H, 7.11.

EXAMPLE 1

(1S*2S*4R*5R*6S*) 2-Amino-4-nitrobicyclo[3.1.0]hexane-2,6-dicarboxylic acid

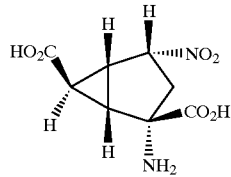

(a) Preparation of (1S*,5R*,6S*)-Ethyl 2-oxobicyclo[3.1.0]hex-3-ene-6-carboxylate.

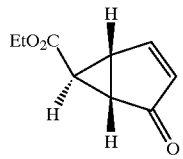

Iodotrimethylsilane (50 g, 250 mmol) was added dropwise to a 0° C. solution of ethyl 2-oxobicyclo[3.1.0]-hexane-6-carboxylate (37 g, 220 mmol) and triethylamine (67 g, 660 mmol) in CH$_2$Cl$_2$ (1L) and stirred for 1 hour. The reaction mixture was diluted with Et$_2$O, washed with saturated aqueous NH$_4$Cl, dried over MgSO$_4$ and concentrated to afford the silyl enolether (97%). To a 0° C. solution of the silyl enolether in CH$_3$CN (300 mL) was added Pd(OAc)$_2$ in one portion. The resulting reaction mixture was allowed to warm to room temperature as it stirred overnight. The reaction mixture was diluted with Et$_2$O filtered through celite and the product adsorbed onto 250 g $SiO_2$. The adsorbed silica was placed on top of a pad of silica, the product eluted with hexanes/EtOAc (4:1), and the resulting pink solid triturated with $Et_2O$ to afford 29.4 g (80%, 177 mmol) of the title compound as a white solid. mp=78–80° C. FDMS: $M^+$=166. Anal. calcd. for $C_9H_{10}O_3$: C, 65.05; H, 6.07. Found: C, 65.34; H, 6.10.

(a1) Alternative preparation of (1S*,5R*,6S*)-ethyl 2-oxobicyclo [3.1.0]-hex-3-ene-6-carboxylate.

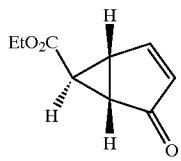

To a flame dried, 3 neck 3L round bottom flask fitted with a $N_2$ inlet and reflux condenser was added a solution of the product from Preparation 2 (102 g, 424 mmol) in 425 mL anhydrous $CH_3CN$, allyl methyl carbonate (99 g, 848 nmol), and $Pd(OAc)_2$ (4.6 g, 20 mmol). The resulting reaction mixture was lowered into a heating bath prewarmed to 70° C. When the internal reaction temperature reached 40° C. a vigorous evolution of gas occurred and ceased after the reaction was complete 30 minutes later. The reaction mixture was diluted with EtOAC (2 L), filtered through $SiO_2$ (≈250 g), and concentrated under reduced pressure to yield 80 g of the crude product. Recrystallization from 10% EtOAc/hexanes afforded pure product, identical in every respect to that obtained in step (a).

(b) Preparation of (1S*,3R*,4R*,5R*,6S*)-Ethyl 2-oxobicyclo [3.1.0]hex-3-ene-oxide-6-carboxylate.

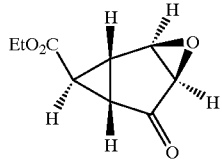

A 0° C. solution of the product of Step (a) (10.1 g, 60.8 mmol) in THF (300 mL) was treated sequentially with DBU (27.75 g, 182 mmol) then tert-butyl hydroperoxide. The resulting reaction mixture was stirred at 0° C. for 1 hour, diluted with $Et_2O$, and partitioned with 1N HCl. The product was extracted with $Et_2O$, dried over $MgSO_4$, and the resulting solid triturated in hexanes/EtOAc (9:1) to afford 9.83 g (89%, 54 mmol) of the title compound. mp=102–104° C. FDMS: $M^+$+1=182. Anal. calcd. for $C_9H_{10}O_4$: C, 59.34; H, 5.53. Found: C, 59.24; H, 5.53.

(c) Preparation of (1S*,4S*,5R*,6S*)-Ethyl 2-oxo-4-hydroxy-bicyclo [3.1.0]hexane-6-carboxylate.

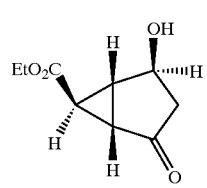

To a stirred degassed suspension of N-acetyl-L-cysteine (25.64 g, 157 mmol), sodium borate.10 $H_2O$ (59.88 g, 157 mmol), and diphenyl-diselenide (0.82 g, 2.62 mmol) in water/EtOH (1:1) (500 mL) was added the product of step (b) in THF (250 mL). Upon complete addition the reaction was stirred at room temperature overnight. The reaction mixture was diluted with $Et_2O$ and partitioned with $H_2O$. The product was extracted with $Et_2O$, washed with $H_2O$ then brine, and dried over $MgSO_4$. The product was purified by HPLC (hexanes/EtOAc) to afford 7.91 g (82%, 43 mmol) of the title compound. mp=60–62° C. FDMS: $M^+$=184. Anal. calcd. for $C_9H_{12}O_4$: C, 58.69; H, 6.57. Found: C, 58.70; H, 6.34.

(d) Preparation of(1S*,2S*,4S*,5R*,6R*)-Diethyl 2-N-t-butyloxycarbonyl-amino-4-hydroxybicyclo[3.1.0]hexane-2,6-dicarboxylate

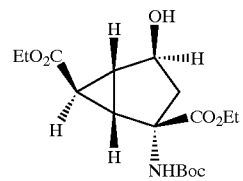

To a stirred solution of the product from step (c) (23.9 g, 130 mmol) in $EtOH/H_2O$ (1:1) (500 mL total volume) was added $(NH_4)_2 CO_3$ (30.4 g, 390 mmol) then KCN (12.7 g, 195 mmol). Upon complete addition, the reaction mixture was warmed at 40° C. until complete. The reaction mixture was cooled to 0° C., acidified to pH=1 with concentrated HCl and the mixture of diastereomeric 5'-spirohydantoins extracted with EtOAc. All organics were combined, washed with brine, dried over $MgSO_4$ and concentrated under reduced pressure to afford a 1:1 mixture of crude hydantoins. The mixture of crude 5'-spirohydantoins (27.9 g, 110 mmol) was warmed under reflux in 2N NaOH (275 mL) for 5 days until the reaction was judged complete by TLC. The reaction mixture was cooled to 0° C., acidified to pH=1 with conc. HCl, and concentrated to dryness in vacuo. The resulting solids were reconstituted in 100% EtOH (500 mL), and chilled to 0° C. $SOCl_2$ (120 g, 1 mol) was then added dropwise to the reaction mixture at a rate to maintain reaction temperature at 10° C. Upon complete addition the reaction was warmed at reflux overnight. The reaction mixture was then concentrated in vacuo and reconstituted in a 1:1 mixture of saturated aqueous $NaHCO_3$:THF (500 mL) total volume. $Boc_2O$ (118 g, 550 mmol) was then added to the reaction mixture in one portion and stirred at room temperature overnight. The reaction mixture was then reduced in vacuo and the crude N-Boc diethylesters extracted with EtOAc. All the organic extracts were combined, washed with $H_2O$ then brine, dried over $K_2CO_3$, and concentrated to yield 120 g of crude product. The two diastereomers are isolated and purified via prep-HPLC (100% hexanes to 50% EtOAc/hexanes) to yield 10.12 g (26%, 28 mmol) of the desired product as a foam. FDMS: $M^+$+1=358. Anal. calcd. for $C_{17}H_{27}NO_7$: C, 57.13; H, 7.61; N, 3.92. Found: C, 56.84; H, 7.64; N, 3.96.

(e) Preparation of (1S*,2S*,4S*,5R*,6R*)-Diethyl 2-N-t-butyloxycarbonyl-amino-4-(p-toluenesulfonyloxy)bicyclo[3.1.0]hexane-2,6-dicarboxylate

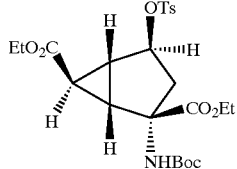

p-Toluenesulfonyl chloride (5.3 g, 28 mmol) was added to a solution of the product of step (d)(5.0 g, 14 mmol) in pyridine (25 mL) and the resulting reaction mixture stirred at room temperature overnight. The reaction mixture was diluted with EtOAc (100 mL) and washed with saturated aqueous CuSO$_4$ to remove the pyridine. The organics were washed with brine, dried over MgSO$_4$ and concentrated under reduced pressure to afford the crude product which was purified by SiO$_2$ chromatography (HPLC: 10% EtOAc/hexanes to 50% EtOAc/hexanes) to obtain 6.55 g (91%, 12.8 mmol) of the desired product as a white foam. FDMS: M$^+$+1=512. Anal. calcd. for C$_{24}$H$_{33}$NO$_9$S: C, 56.35; H, 6.50; N, 2.74. Found: C, 56.48; H, 6.44; N, 2.60.

(f) Preparation of (1S*,2S*,4R*,5R*,6S*)-Diethyl 2-N-t-butyloxy-carbonylamino-4-azidobicyclo[3.1.0]hexane-2,6-dicarboxylate.

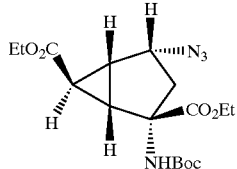

A solution of the product from step (e) (6.35 g, 12.4 mmol) and NaN$_3$ (2.42 g, 37.2 mmol) in DMSO (15 mL) was warmed at 35° C. for 3 days. The reaction mixture was diluted with H$_2$O and the product extracted with EtOAc. All organics were combined, washed with brine, dried over MgSO$_4$, and concentrated under reduced pressure to yield the crude azide which was purified by vacuum filtration through SiO$_2$ (20% EtOAc/hexanes to 50% EtOAc/hexanes) to afford 4.68 g (98t, 12.2 mmol) of the desired product as a waxy solid. FDMS: M$^+$+1=512. Anal. calcd. for C$_{17}$H$_{26}$N$_4$O$_6$.0.1 hexanes: C, 54.06; H, 7.06; N, 14.33. Found: C, 53.94; H, 6.88; N, 14.30.

(g) Preparation of(1S*,2S*,4R*,5R*,6S*)-Diethyl 2-N-t-butyloxycarbonyl-4-aminobicyclo[3.1.0]hexane-2,6-dicarboxylate.

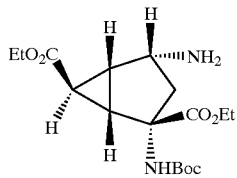

Triphenyl-phosphine (2.90 g, 11 mmol) was added in one portion to a solution of the product of step (f) (3.5 g, 9.2 mmol) in THF/H$_2$O (5:1) and stirred at room temperature overnight. The reaction mixture was diluted with EtOAc and washed with 0.5N NaOH (3×). The organics were combined, washed with H$_2$O then brine, dried over K$_2$CO$_3$, concentrated under reduced pressure and purified by SiO$_2$ chromatography (HPLC: SiO$_2$ (10% EtOAc/hexanes to 50% EtOAc/hexanes) to afford 2.03 g (62%, 5.7 mmol) of the desired product as a foam. FDMS: M$^+$+1=357. Anal. calcd. for C$_{17}$H$_{28}$N$_2$O$_6$: C, 57.30; H, 7.92; N, 7.86. Found: C, 57.02; H, 7.73; N, 7.72.

(h) Preparation of (1S*,2S*,4R*,5R*,6S*) Diethyl 2-t-butyloxycarbonylamino-4-nitrobicyclo[3.1.0]hexane-2,6-dicarboxylic acid

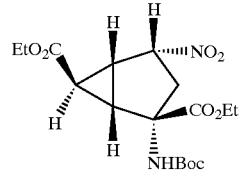

A 0° C. solution of product of step (g) (1.1 g, 3.1 mmol) in CHCl$_3$ (30 mL) was treated in one portion with 3-chloroperoxybenzoic acid (80%) (2.0 g, 9.3 mmol) and stirred at room temperature overnight. 2-Propanol was added to the reaction mixture to quench the oxidant and the subsequent reaction mixture partitioned between aqueous NaHCO$_3$/EtOAc. The product was extracted with EtOAc, washed with brine and dried over MgSO$_4$. Upon reduction of volume under reduced pressure, a white solid precipitated from the solution. The solid was removed by vacuum filtration and identified as 3-chlorobenzoic acid. The filtrate was concentrated and purified by PC-TLC (10% EtOAc/hexanes to 100% EtOAc) to afford 0.11 g (0.28 mmol, 9.2%) of the desired product as a white foam which contained a 0.10% impurity of 3-chlorobenzoic acid. FDMS: M$^+$+1= 387. IR (KBr): 3371, 2983, 1729, 1553, 1508, 1369, 1282, 1166 cm$^{-1}$. $^1$H NMR (CDCl$_3$): δ1.27 (2t, J=7 Hz, 6H), 1.43 (s, 9H), 2.02 (m, 1H), 2.35 (m, 2H), 2.55 (m, 1H), 3.18 (m, 1H), 4.14 (q, J=7 Hz, 2H), 4.23 (m, 2H), 5.36 (m, 1H), 5.46 (m, 1H), 7.42 (m, 0.1H, 3-chlorobenzoic acid), 7.61 (m, 0.1H, 3-chlorobenzoic acid), 8.0 (m, 0.2H, 3-chlorobenzoic acid). Anal. calcd. for C$_{17}$H$_{26}$N$_2$O$_8$.0.1 eq 3-chlorobenzoic acid: C, 52.88; H, 6.64; N, 6.97. Found: C, 52.52; H, 6.47; N, 6.57.

(i) Preparation of Diethyl (1S*,2S*,4R*,5R*,6S*) 2-amino-4-nitrobicyclo [3.1.0]-hexane-2,6-dicarboxylic acid

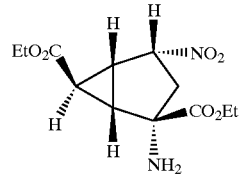

A 0° C. solution of the product of step (h) (0.19 g, 0.49 mmol) in EtOAc (10 mL) was purged with anhydrous HCl gas until the solution reached saturation. The resulting reaction mixture was allowed to warm as it stirred for 2 hours and then concentrated to dryness under reduced pressure. The solids were dissolved in saturated NaHCO$_3$ (aq) and the product extracted with EtOAc. All organics were combined, washed with brine, dried over K$_2$CO$_3$, concentrated under reduced pressure and purified by PC-TLC (10% EtOAc/hexanes to 50% EtOAc) to afford 0.10 g (0.35 nmol, 71%) of the desired product. FDMS: M$^+$+1=287. $^1$H NMR (CDCL$_3$): δ1.27 (t, J=7 Hz, 3H) , 1.34 (t, J=7 Hz, 3H), 1.81 (br s, 2H), 1.94 (dd, J=14 Hz, J=5 Hz, 1H), 2.28 (m, 2H) , 2.58 (m, 2H), 4.14 (q, J=7 Hz, 2H) , 4.26 (q, J=7 Hz, 2H), 5.26 (m, 1H). IR (film): 2981, 1718, 1545, 1368, 1273, 1184 cm$^{-1}$. Anal. calcd. For $C_{12}H_{18}N_2O_6$.0.1 eq $H_2O$: C, 50.03; H, 6.37; N, 9.72. Found: C, 49.91; H, 6.42; N, 9.38.

(j) Preparation of (1S*,2S*,4R*,5R*,6S*) 2-Amino-4-nitrobicyclo [3.1.0]hexane-2,6-dicarboxylic acid

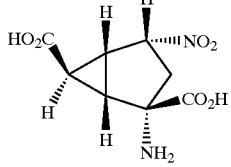

A solution of the product of step (i) (0.08 g, 0.28 mmol) in a 1:1 mixture of 1N NaOH/THF (6 mL total volume) was stirred at room temperature overnight. The reaction mixture was adjusted to pH=7 with 1N HCl and concentrated to dryness. The resulting solids were reconstituted in $H_2O$, adjusted to pH=12 with 1N NaOH and applied to Bio-Rad® AG1-X8 anion exchange resin (acetate form converted to hydroxide form). The product was eluted with 3N acetic acid to afford 0.04 g (64%, 0.18 mmol) of the title compound. mp=dec >250° C. FDMS: M$^+$+1=231. IR (KBr): 3051, 1701, 1616, 1554, 1451, 1395, 1312, 1274, 1194, 1156, 916 cm$^{-1}$. Anal. calcd. For $C_8H_{10}N_2O_6$: C, 41.75; H, 4.38; N, 12.17. Found: C, 41.77; H, 4.10; N, 11.89.

What is claimed is:

1. A compound of the formula

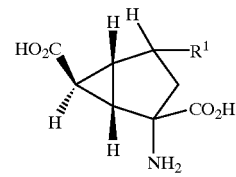

in which $R^1$ represents $NO_2$; or a non-toxic metabolically labile ester or amide thereof; or a pharmaceutically acceptable salt thereof.

2. A compound according to claim 1 in which the compound is (1S*,2S*,4R*,5R*,6S*) 2-Amino-4-nitrobicyclo [3.1.0]hexane-2,6-dicarboxylic acid.

3. A pharmaceutical formulation, which comprises a compound as claimed in claim 1 and a pharmaceutically acceptable carrier, diluent or excipient.

4. A method of modulating metabotropic glutamate receptor function in a mammal which comprises administering an effective amount of a compound of formula I; or a non-toxic metabolically labile ester or amide thereof; or a pharmaceutically acceptable salt thereof.

* * * * *